United States Patent
Gordy et al.

(10) Patent No.: US 7,922,764 B2
(45) Date of Patent: Apr. 12, 2011

(54) BIOPROSTHETIC HEART VALVE WITH POLYPHOSPHAZENE

(75) Inventors: Thomas A. Gordy, Newnan, GA (US); Neng S. Ung, Lincolnshire, IL (US); Ulf Fritz, Hirschhorn (DE); Roman Denk, Weidenstetten (DE)

(73) Assignee: Celonova Bioscience, Inc., Peachtree City, GA (US)

( * ) Notice: Subject to any disclaimer, the term of this patent is extended or adjusted under 35 U.S.C. 154(b) by 592 days.

(21) Appl. No.: 11/869,889

(22) Filed: Oct. 10, 2007

(65) Prior Publication Data

US 2008/0086205 A1   Apr. 10, 2008

Related U.S. Application Data

(60) Provisional application No. 60/828,840, filed on Oct. 10, 2006.

(51) Int. Cl.
*A61F 2/24* (2006.01)
*C08G 79/02* (2006.01)

(52) U.S. Cl. .................................. 623/2.42; 528/399

(58) Field of Classification Search ............ 623/2, 2.42; 528/399
See application file for complete search history.

(56) References Cited

U.S. PATENT DOCUMENTS

| | | |
|---|---|---|
| 4,311,736 A | 1/1982 | Leong |
| 4,318,947 A | 3/1982 | Joung |
| 4,341,844 A | 7/1982 | Leong |
| 4,424,395 A | 1/1984 | Strom |
| 4,451,647 A | 5/1984 | Allcock et al. |
| 4,480,642 A | 11/1984 | Stoy et al. |
| 4,507,123 A | 3/1985 | Yoshida |
| 4,579,880 A | 4/1986 | Ohashi |
| 4,592,755 A | 6/1986 | Penton et al. |
| 4,798,876 A | 1/1989 | Gould et al. |
| 4,880,622 A | 11/1989 | Allcock et al. |
| 4,883,699 A | 11/1989 | Aniuk et al. |
| 4,911,691 A | 3/1990 | Aniuk et al. |
| 4,975,280 A | 12/1990 | Schacht et al. |
| 5,238,569 A | 8/1993 | Soria et al. |
| 5,308,701 A | 5/1994 | Cohen et al. |
| 5,439,446 A | 8/1995 | Barry |
| 5,548,060 A | 8/1996 | Allcock et al. |
| 5,552,159 A | 9/1996 | Mueller et al. |
| 5,605,696 A | 2/1997 | Eury et al. |
| 5,634,946 A | 6/1997 | Slepian |
| 5,707,597 A | 1/1998 | Andrianov et al. |
| 5,716,981 A | 2/1998 | Hunter et al. |
| 5,788,979 A | 8/1998 | Alt et al. |
| 5,814,704 A | 9/1998 | Andrianov et al. |
| 5,873,904 A | 2/1999 | Ragheb et al. |

(Continued)

FOREIGN PATENT DOCUMENTS

CA         1252253         4/1989

(Continued)

OTHER PUBLICATIONS

Steely, Lee Brent, "Hydrophobic and Hydrophilic Control in Polyphosphazene Materials," Ph.D. Thesis in Chemistry, Pennsylvania State University, Aug. 2007.

(Continued)

*Primary Examiner* — Duc Truong

(57) ABSTRACT

This disclosure encompasses a bioprosthetic heart valve having a polyphosphazene polymer such as poly[bis(trifluoroethoxy)phosphazene], which exhibits improved antithrombogenic, biocompatibility, and hemocompatibility properties. A method of manufacturing a bioprosthetic heart valve having a polyphosphazene polymer is also described.

24 Claims, 4 Drawing Sheets

U.S. PATENT DOCUMENTS

| | | | |
|---|---|---|---|
| 5,886,026 | A | 3/1999 | Hunter et al. |
| 5,914,388 | A | 6/1999 | Allcock |
| 5,980,972 | A | 11/1999 | Ding |
| 5,997,301 | A | 12/1999 | Linden |
| 6,007,573 | A | 12/1999 | Wallace et al. |
| 6,077,916 | A | 6/2000 | Laurencin |
| 6,207,171 | B1 | 3/2001 | Payne et al. |
| 6,235,061 | B1 | 5/2001 | Laurencin et al. |
| 6,254,634 | B1 | 7/2001 | Anderson |
| 6,273,913 | B1 | 8/2001 | Wright et al. |
| 6,319,984 | B1 | 11/2001 | Song et al. |
| 6,346,110 | B2 | 2/2002 | Wu |
| 6,432,128 | B1 | 8/2002 | Wallace et al. |
| 6,485,514 | B1 | 11/2002 | Wrenn, Jr. |
| 6,503,556 | B2 | 1/2003 | Harish et al. |
| 6,506,411 | B2 | 1/2003 | Hunter et al. |
| 6,569,195 | B2 | 5/2003 | Yang et al. |
| 6,652,575 | B2 | 11/2003 | Wang |
| 6,669,719 | B2 | 12/2003 | Wallace et al. |
| 2001/0014717 | A1 | 8/2001 | Hossainy et al. |
| 2001/0029351 | A1 | 10/2001 | Faletico et al. |
| 2002/0005206 | A1 | 1/2002 | Faletico et al. |
| 2002/0094440 | A1 | 7/2002 | Llanos et al. |
| 2002/0111590 | A1 | 8/2002 | Davila et al. |
| 2002/0119202 | A1 | 8/2002 | Hunter et al. |
| 2002/0133183 | A1 | 9/2002 | Lentz et al. |
| 2002/0165608 | A1 | 11/2002 | Llanos et al. |
| 2003/0004568 | A1 | 1/2003 | Ken et al. |
| 2003/0060877 | A1 | 3/2003 | Falotico et al. |
| 2003/0065345 | A1 | 4/2003 | Weadock |
| 2003/0065377 | A1 | 4/2003 | Davila et al. |
| 2003/0099683 | A1 | 5/2003 | Grunze |
| 2003/0153983 | A1 | 8/2003 | Miller et al. |
| 2003/0153985 | A1 | 8/2003 | Lee |
| 2003/0157142 | A1 | 8/2003 | Nagel et al. |
| 2005/0136093 | A1 | 6/2005 | Denk |
| 2005/0209629 | A1 | 9/2005 | Kerr et al. |
| 2006/0008529 | A1 | 1/2006 | Meyerhoff et al. |
| 2006/0088476 | A1 | 4/2006 | Harder et al. |
| 2006/0147895 | A1 | 7/2006 | Purdum |
| 2006/0201673 | A1 | 9/2006 | Welton et al. |
| 2006/0246109 | A1 | 11/2006 | Hossainy et al. |
| 2007/0292429 | A1 | 12/2007 | Brady et al. |
| 2008/0003256 | A1 | 1/2008 | Martens et al. |
| 2008/0102029 | A1 | 5/2008 | Fritz et al. |

FOREIGN PATENT DOCUMENTS

| | | | |
|---|---|---|---|
| DE | 19613048 A1 | 10/1996 | |
| DE | 19613048 C2 | 10/1996 | |
| DE | 10019982 A1 | 10/2001 | |
| DE | 10100961 A1 | 8/2002 | |
| EP | 0150699 A2 | 8/1985 | |
| EP | 0286709 A1 | 10/1988 | |
| EP | 0706376 B1 | 6/1997 | |
| EP | 0804909 A2 | 11/1997 | |
| EP | 0970711 A2 | 1/2000 | |
| EP | 1112094 B1 | 7/2001 | |
| EP | 1179353 A1 | 2/2002 | |
| EP | 1337285 A1 | 8/2003 | |
| EP | 1426075 A | 6/2004 | |
| EP | 1488817 A1 | 12/2004 | |
| JP | 58079915 A | 5/1983 | |
| JP | 4337328 A | 11/1992 | |
| WO | 8809664 A1 | 12/1988 | |
| WO | 9321858 A1 | 11/1993 | |
| WO | 9502628 A1 | 1/1995 | |
| WO | WO 9528150 A | 10/1995 | |
| WO | 9528966 A1 | 11/1995 | |
| WO | 9600103 A1 | 1/1996 | |
| WO | 9604015 A1 | 2/1996 | |
| WO | 9625176 A1 | 8/1996 | |
| WO | 9625897 A2 | 8/1996 | |
| WO | 9629059 A1 | 9/1996 | |
| WO | WO 9800531 A | 1/1998 | |
| WO | 9843618 A2 | 10/1998 | |
| WO | 9852605 A1 | 11/1998 | |
| WO | 9856312 A1 | 12/1998 | |
| WO | 9909088 A2 | 2/1999 | |
| WO | 9916416 A2 | 4/1999 | |
| WO | 9916477 A2 | 4/1999 | |
| WO | 9916477 A3 | 4/1999 | |
| WO | 9942147 A1 | 8/1999 | |
| WO | 9952356 A1 | 10/1999 | |
| WO | 0032238 | 6/2000 | |
| WO | WO 0056254 A | 9/2000 | |
| WO | 0061204 A1 | 10/2000 | |
| WO | 0136008 A2 | 5/2001 | |
| WO | 0145763 A1 | 6/2001 | |
| WO | 0149340 A1 | 7/2001 | |
| WO | 0170296 A1 | 9/2001 | |
| WO | 0180919 A2 | 11/2001 | |
| WO | 0187368 A1 | 11/2001 | |
| WO | 0187372 A1 | 11/2001 | |
| WO | WO 0180919 A3 | 11/2001 | |
| WO | 0224247 A1 | 3/2002 | |
| WO | WO 02064666 A2 | 8/2002 | |
| WO | WO 02064666 A3 | 8/2002 | |
| WO | WO 03015719 A | 2/2003 | |
| WO | WO 2004004795 A | 1/2004 | |
| WO | 2004011055 A2 | 2/2004 | |
| WO | WO 2004048432 A | 6/2004 | |
| WO | WO 2004060283 A | 7/2004 | |
| WO | WO 2006046155 A2 | 5/2006 | |
| WO | WO 2007056316 A | 5/2007 | |

OTHER PUBLICATIONS

Barrett, Eric W., "Polyphosphazenes for Biomedical Devices and Other Applications," Ph.D. Thesis in Chemistry, Pennsylvania State University, Dec. 2005.

Guigley, Kevin S., "Hydrogen Bonded Polymer Blends," Ph.D. Thesis in Materials Science and Engineering, Pennsylvania State University, Dec. 2001.

Welna, Daniel Thomas, "Design, Synthesis, and Characterization of Polymeric Materials for uses in Energy Storage Applications," Ph.D. Thesis in Chemistry, Pennsylvania State University, Aug. 2006.

Maher, Andrew Elessar, "Synthesis and Characterization of Mixed-Substituent Poly(Organophosphazenes)," Ph.D. Thesis in Chemistry, Pennsylvania State university, May 2004.

Nielsen, Gunmar D., et al., "Sensory irritation mechanisms investigated from model compounds: trifluoroethanol, hexafluoroisopropanol and methyl hexafluoroisopropyl ether," 1996, Arch Toxicol, 70:319-328.

Kumar, Yogesh, et al., "Molten-globule like partially folded states of human serum albumin induced by fluoro and alkyl alcohols at low pH," Archives of Biochemistry and Biophysics, 426 (2004) 3-10.

Hansen, Charles M., "Hansen Solubility Parameters—A User's Handbook," 2000 by CRC Press LLC.

Gast, Klaus, et al., "Fluoroalcohol-induced structural changes of proteins: some aspects of cosolvent-protein interactions," Eur Biophys J (2001 20: 273-283).

Kumar, Yogesh, et al., "Influence of Fluoro, Chloro and Alkyl Alcohols on the Folding Pathway of Human Serum Albumin," J. Biochem, (2005), 138, 335-341.

Rothemund, Sven, et al., "Temperature coefficients of amide proton NMR resonance frequencies in trifluoroethanol: A monitor of intramolecular hydrogen bonds in helical peptides?," Journal of Biomecular NMR, 8 91996) 93-97.

Yao, Shenggen, et al., "Peptide self-association in aqueous trifluoroethanol monitored by pulsed field gradient NMR diffusion measurements," Journal of Biomolecular NMR, 16:109-111, 2000.

Contreras, Miguel Angel, et al., "Temperature coefficients of peptides dissolved in hexafluoroisopropanol monitor distortions of helices," Letters in Peptide Science, 4 (1979) 29-39.

Roccatano, Danilo, et al., "Effect of hexafluoroisopropanol alcohol on the structure of melittin: A molecular dynamics simulation study," Protein Science, 2005, 14:2582-2589.

Hori, Yoshio, et al., Functional Analysis of the Tissue-Engineered Stomach Wall, Artificial Organs, 2002, 26 (10):868-893, Blackwell Publishing, Inc., International Society for Artificial Organs.

Allcock, Harry, R., et al., "Antibacterial activity and mutagenicity studies of water-soluble phosphazene high polymers," Biomaterials, vol. 13, No. 2, pp. 857-862 (1992), Butterworth-Heinemann Ltd., USA.

Mrowietz, C., et al., "Haemocompatibility of polymer-coated stainless steel stents as compared to uncoated stents," Clinical Hemorheology and Microcirculation, 32 (2005) 89-103.

Cohen, Smadar, et al., "Design of Synthetic Polymeric Structures for Cell Transplantation and Tissue Engineering," Clinical Materials, vol. 13, 3-10 91993), Elsevier Science Publishers Ltd., England.

Huang, Yangmin, et al., "Long-term biocompatibility evaluation of a novel polymer-coated stent in a porcine coronary stent model," Therapy and prevention, 2003, Coronary Artery Disease, vol. 14, No. 5, 401-408.

Richter, Goetz M., et al., "A New Polymer Concept for Coating of Vascular Stents Using PTFEP (poly(bis (trifluoroethoxy)phosphazene) to Reduce Thrombogenicity and Late In-Stent Stenosis," Investigative Radiology, Apr. 2005, vol. 40, No. 4, 210-218.

Welle, Alexander, "Competitive plasma protein adsorption on modified polymer surfaces monitored by quartz crystal microbalance technique," J. Biomater. Sci. Polymer Edn. (2004) vol. 15, No. 3, pp. 357-370.

Welle, Alexander, et al., "Blood Compatibility of Poy[bis(trifluoroethoxy)phosphazene]," Institute of Applied Physical Chemistry, JAMP, vol. 4, 6-10, (2000), University of Heidelberg, Germany.

Reichert, W. M., et al., "Polyphosphazenes: Effect of molecular motions on thrombogenesis," Journal of Biomedical Materials Research, (1982), vol. 16, 301-312.

Lopez, Gabriel P., et al., "Glow Discharge Plasma Deposition of Tetraethylene Glycol Dimethyl Ether for Fouling-Resistant Biomaterial Surfaces," J. of Biomedical Materials Research, vol. 26, 415-439 91992), John Wiley & Sons, Inc., USA.

Laurencin, Cato T., et al., "Use of polyphosphazenes for skeletal tissue regeneration," J. Biomedical Materials Research, vol. 27, No. 7, pp. 963-973 (1993), John Wiley & Sons, Inc., USA.

IBIM, Sobrasua M., et al., "Controlled Macromolecule Release from Poly(phosphazene) Matrices," Journal of Controlled Release, vol. 40, 31-39 (Jun. 1996), Elsevier Science B.V.

Veronese, Francesco M., et al., "Polyphosphazene Membranes and Microspheres in Periodontal Diseases and Implant Surgery," Biomaterials, vol. 20, 91-98 91999), Elsevier, USA.

Vinogradova, S.V., et al., "Open-chain Poly(organophosphazenes). Synthesis and Properties," Russian Chemical Reviews, vol. 67, 515-534 (1998), Russian Academy of Sciences and Turpion Ltd.

Welle, A., et al., "Plasma Protein Adsorption and Platelet Adhesion on Poly[bis(trifluoroethoxy)phosphazene] and reference material surfaces," appeared in J. Colloid Intef. Sci., 197, 263-274, (1998).

Barrett, Eric W., et al., "Patterning Poly(organophosphazenes) for Selective Cell Adhesion Applications," Biomacromolecules, (2005), 6, 1689-1697.

Acta Polymerica 37 (1986) No. 4:203-208.

Acta Polymerica 30 (1979), pp. 245-248.

Acta Polymerica 36 (1985), pp. 627-631.

Kingshott, P., "Surfaces that Resist Bioadhesion," Current Opinion in Solid State and Materials Science, vol. 4, 403-412 (1999), Pergamon.

Waksman, R., "Vascular Brachytherapy: Applications in the Era of Drug-Eluting Stents," Reviews in Cardiovascular Medicine, vol. 3, S23-S30 (2002), MedReviews, LLC, USA.

Kajiwara, M., "The Study of the Cultivation of Chinese Hamster Ovary and Bows Cell Lines," Phosphorus, Sulfur, and Silicon, vol. 76, pp. 163-166 (1993), Gordon and Breach Science Publishers S.A., USA.

Ph. Potin & R. DeJaeger, "Review: Polyphosphazenes: Synthesis, Structures, Properties, Applications," European Polymer Journal, vol. 27, 341-348 (991), Pergamon Press, Great Britain.

Lemmouchi, Y., et al., "Biodegradable Polyphosphazenes for Drug Delivery," Macromolecular Symposia, vol. 123, 103-112 (Sep. 1997) Wiley VCH, Weinheim, Germany.

Chaikof, Elliott L., "The Development of Prosthetic Heart Valves—Lessons in Form and Function," Oct. 4, 2007, vol. 357:1368-1371, No. 14.

Allcock, Harry R., Poly(organophosphazenes)-Unusual New High Polymers, Angew. Chem. Int. Ed. Engl. 16, 147-156 (1977).

Caliceti, Paolo, et al., "Polyphosphazene microspheres for insulin delivery," International Journal of Pharmaceutics, 211 (2000) 57-65.

International Search Report and Written Opinion (PCT/US2007/080969), International Searching Authority.

International Search Report and Written Opinion (PCT/US2007/082659), International Searching Authority.

Kumbar, Sangamesh G., et al., In Vitro and In Vivo Characterization of Biodegradable Poly(organophosphazenes) for Biomedical Applications, Journal of Inorganic and Organometallic Polymers and Materials, vol. 16, No. 4, Dec. 2006, pp. 365-385.

Honarkar, Hengameh, et al., "Applications of Inorganic Polymeric Materials, III: Polyphosphazenes,"Monatshefte fur Chemie 138, 923-933 (2007).

Allcock, H., "Phosphazene high polymers with bioactive substitutent groups: prospective anesthetic aminophosphazenes," Macromolecules, 15(3):689-693 (1982).

Ambrosio, et al., "Novel Polyphosphazene-Hydroxyapatite Composites as Biomaterials," IEEE Engineering in Medicine and Biology Magazine, 22(5):18-26 (Sep. 5, 2003).

Chaubal, M., et al., "Polyphosphates and other phosphorus-containing polymers for drug delivery applications," Critical Reviews™ in Therapeutic Drug Carrier Systems, 20(4):295-315 (2003).

El-Amin, et al., "The Biocompatibility of Biodegradable Glycine Containing Polyphosphazenes: A Comparative Study in Bone," Journal of Inorganic and Organometallic Polymers and Materials, 2006, vol. 16, No. 4, pp. 387-396.

Goedemoed, J., et al "Development of implantable antitumor devices based on polyphosphazenes," Die Makromolekulare Chemie, 19:341-365 (1988).

Henry, R., et al., "Topical lidocaine-prilocaine spray for the treatment of premature ejaculation," International Journal of Impotence Research, 15(4):277-281 (2003).

Laurencin, C., et al., "Controlled release using a new bioerodible polyphosphazene matrix system," Journal of Biomedical Materials Research, 21:1231-1246 (1987).

International Search Report and Written Opinion (PCT/US2007/082426), International Searching Authority.

International Search Report and Written Opinion (PCT/US2007/082430), International Searching Authority.

International Search Report and Written Opinion (PCT/US2007/082651), International Searching Authority.

International Search Report and Written Opinion (PCT/US2007/082672), International Searching Authority.

International Search Report and Written Opinion (PCT/US2007/083043), International Searching Authority.

International Search Report and Written Opinion (PCT/US2007/083199), International Searching Authority.

International Search Report and Written Opinion (PCT/US2007/083209), International Searching Authority.

International Search Report and Written Opinion (PCT/US2007/083216), International Searching Authority.

De Jaeger, Roger, et al., "Poly(organophosphazene)s and Related Compounds: Synthesis, Properties and Applications," Prog. Polym. Sci., vol. 23, 179-276 (1998), Pergamon Press, Great Britain.

De Scheerder, Ivan K., et al., "Angiopeptin Loaded Stents Inhibit the Neointimal Reaction Induced by Polymer Coated Stents Implanted in Porcine Coronary Arteries," Abstract 772-6, pp. 286A, JACC (Feb. 1995). (Abstract).

Grunze, Michael, et al., 32P-labeled polyphosphazenes, 1999, Chemical Abstracts, vol. 130, No. 20: 272061.

Macromolecules 1987, vol. 20, pp. 782-789.

Mark, James E., et al., "Polyphosphazenes", Inorganic Polymers, 1992, pp. 61-139, XP000866367, pp. 95-117.

McCaffrey, R.R. et al., "Synthesis, Casting, and Diffusion Testing of Poly[bis(tri-fluoroethoxy)phosphazene] Membranes," J. of Membrane Science, vol. 28, 47-67 (1986), Elsevier Science Publishers B.V., Netherlands.

Welle, A. et al., "Polyphosphazenes as antithrombotic coatings for prostetic heart valves," Presented at 19th Annual Meeting of the Adhesion Society, Myrtle Beach, SC, 4 pages (Feb.1996).

A
B

A          B

BIOPROSTHETIC HEART VALVE WITH POLYPHOSPHAZENE

CROSS-REFERENCE TO RELATED APPLICATIONS

This application claims the benefit of U.S. Provisional Patent Application No. 60/828,840, filed Oct. 10, 2006, the entirety of which is hereby incorporated by reference.

FIELD OF THE INVENTION

The present invention relates to bioprosthetic implants such as bioprosthetic heart valves having antithrombogenic, biocompatibility, and hemocompatibility properties.

BACKGROUND OF THE INVENTION

Heart valves play a pivotal role in circulatory function by maintaining the unidirectional flow of blood by opening and closing as a result of pressure differences on either side. However, natural heart valves may become dysfunctional from a variety of pathological causes such as stenosis and incompetence. A stenotic heart valve does not open fully due to stiffening of the valve tissue, thus more work is required for the heart to force blood through the valve. An incompetent valve causes inefficient blood circulation by permitting the flow of blood back into its originating chamber.

In many patients, a diseased heart valve can be replaced by a prosthetic heart valve. Prosthetic valves can be classified broadly into two principal types: mechanical and bioprosthetic. Mechanical valves are constructed exclusively from synthetic materials and are excellent in terms of durability. Traditional mechanical heart valves may produce good flow performance characteristics and potentially last longer than bioprosthetic valves, yet mechanical valves have a number of disadvantages. Mechanical heart valves require long-term or even lifetime anti-coagulation therapy to reduce the risk of thrombosis and embolism. Such a regimen effectively makes patients with mechanical heart valves borderline hemophiliacs. Patients with mechanical heart valves further require strict dietary and/or activity constraints, and the mechanical heart valve may produce an annoying valve "clicking" sound.

Bioprosthetic or biological valves include any valve that incorporates biological tissue, and themselves can be classified broadly into two principle types: the "graft-type," in which substantially the entire valve is grafted from another individual; and the "tissue-type," which are constructed in whole or in part with natural-tissue parts, such as valve leaflets. For the graft-type, an actual heart valve is retrieved from either a deceased human (homograft or allograft) or from a slaughtered pig or other mammal (xenograft). The retrieved valve can be preserved and/or sterilized, for example, homografts are typically cryopreserved and xenografts are typically cross-linked, typically in a glutaraldehyde solution.

Tissue-type bioprosthetic heart valves comprise assemblies having various amounts of biological material incorporated. Biological tissue typically is harvested from heart valves or from the pericardial sac of bovine (cattle), equine (horse), porcine (pig), or other mammalian sources. For example, some of these valves include leaflets derived from natural material (typically porcine) and still include the natural supporting structure or ring of the aortic wall. In other valves, leaflets derived from natural material (typically bovine pericardium) are trimmed and attached to a synthetic, roughly annular structure or ring that mimics the function of the natural aortic wall. In still other valves, both the leaflets and the annular support ring are formed of biopolymers such as collagen and/or elastin. All these valves, which include some biological tissue or biopolymers, are referred to herein as bioprosthetic valves, and include such assemblages as so-called "stented" valves which includes a stent and a biological valve member.

Bioprosthetic heart valves generally are less durable than mechanical valves, but they can alleviate some of the risks associated with mechanical valves, such as reducing the risk of forming blood clots, possible thrombosis and embolism, and/or the need for long-term anticoagulation therapy. Thus, problems related to the requirement for anticoagulants are usually short term with tissue-type valves and their failure is seldom abrupt. In addition, bioprosthetic heart valves are closer in design to the natural valve, have better hemodynamics, and do not cause damage to blood cells. However, biological heart valves are not without risk. Biological heart valves are susceptible to degeneration and/or calcification as a result of glutaraldehyde fixation, mechanical stresses, and the deposition of calcium phosphate on surfaces. Due to the degeneration of biological heart valves, such valves usually last about 10 to 15 years, often requiring additional surgery to replace or repair the valve.

Therefore, there exists a need for an improved biological or bioprosthetic heart valves that have good antithrombogenic, biocompatibility, and hemocompatibility properties. Such bioprosthetic heart valves should be less susceptible to degeneration and/or calcification and significantly improve the overall lifespan of the implant.

BRIEF SUMMARY OF THE INVENTION

The present invention provides for a bioprosthetic heart valve comprising a biological tissue and a polyphosphazene represented by formula (I):

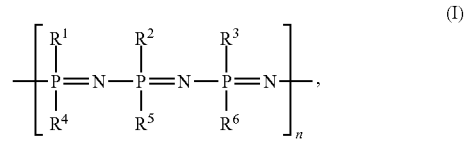

(I)

wherein n is 2 to ∞; and $R^1$ to $R^6$ are groups which are each selected independently from alkyl, aminoalkyl, haloalkyl, thioalkyl, thioaryl, alkoxy, haloalkoxy, aryloxy, haloaryloxy, alkylthiolate, arylthiolate, alkylsulphonyl, alkylamino, dialkylamino, heterocycloalkyl comprising one or more heteroatoms selected from nitrogen, oxygen, sulfur, phosphorus, or a combination thereof, or heteroaryl comprising one or more heteroatoms selected from nitrogen, oxygen, sulfur, phosphorus, or a combination thereof.

The present invention also provides for a method of manufacturing a bioprosthetic heart valve, comprising providing a biological tissue and contacting the biological tissue with a polyphosphazene of formula (I), illustrated herein. For example, the polyphosphazene of formula (I) may be applied to the surface of the bioprosthetic heart valve by simply contacting the surface of the bioprosthetic heart valve with the polyphosphazene, in which the polyphosphazene may be in any form and is typically in solution, with or without other components such as a surfactant or fixing agent.

The present invention further provides for a method of manufacturing a bioprosthetic heart valve comprising: combining a poly[bis(trifluoroethoxy)phosphazene] polymer, a fixing agent, a surfactant, and a poly[bis(trifluoro-ethoxy)

phosphazene] soluble organic solvent to form a solution; and applying (contacting) the solution to the bioprosthetic implant. The trifluoroethoxy moiety of this polyphosphazene is the 2,2,2-trifluoroethoxy group, $OCH_2CF_3$.

The present invention also provides for a method of treating a bioprosthetic heart valve comprising contacting tissue in the valve with a polyphosphazene represented by formula (I), as disclosed above. The present invention further provides for a bioprosthetic implant comprising: a biological tissue; and a polyphosphazene, for example, a poly[bis(trifluoroethoxy) phosphazene] polymer, applied to the biological tissue.

The present invention also provides for a bioprosthetic implant comprising biological tissue and a polyphosphazene according to formula (I), as disclosed above, wherein the polyphosphazene is incorporated into the implant by at least one of coating the tissue and impregnation of the tissue.

This invention further provides for a method of improving the antithrombogenic, biocompatibility, or hemocompatibility properties of a bioprosthetic heart valve, comprising contacting the bioprosthetic heart valve with a polyphosphazene of formula (I), which is provided herein, wherein the polyphosphazene is coated, diffused, impregnated, grafted, or any combination thereof, into or onto the bioprosthetic heart valve.

In another aspect this invention provides a bioprosthetic heart valve comprising a mammalian heart valve and a poly[bis(trifluoroethoxy)phosphazene]. This invention also provides for a method of making a bioprosthetic heart valve comprising:
  providing a mammalian heart valve; and
  contacting the mammalian heart valve with a poly[bis(trifluoroethoxy)-phosphazene];
  wherein the poly[bis(trifluoroethoxy)phosphazene] is coated, diffused, impregnated, grafted, or any combination thereof into or onto the mammalian heart valve.

DETAILED DESCRIPTION OF THE INVENTION

Figure 1:
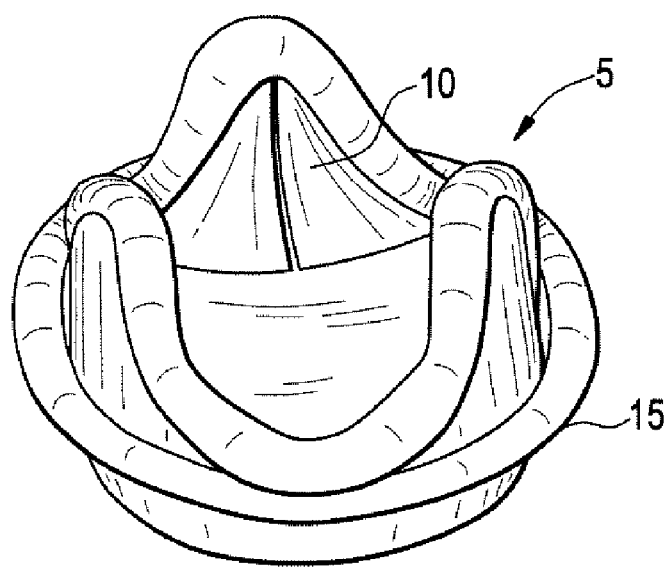
FIG. 1 is a perspective view of a porcine graft-type (xenograft) heart valve that may be treated as disclosed herein.

The present invention relates to bioprosthetic heart valve implants that include a bioprosthetic heart valve comprising a phosphazene-based polymer, that is, a polyphosphazene. Additionally, the present invention provides for a method of manufacturing a bioprosthetic heart valve comprising a polyphosphazene. As used herein, with respect to heart valves, the word "treated" is considered broader than terms such as "coated." A treated heart valve is a heart valve that has been contacted with the polyphosphazene in any manner, without regard to a particular mechanism by which the polyphosphazene interacts with the heart valve when contacted, as long as some polyphosphazene is retained in or on the treated heart valve. For example in treated heart valves, rather than merely collecting or layering on the surface as in "coating," the polyphosphazene may also diffuse into or otherwise be impregnated into or grafted to the biological tissue, although there is no requirement for any particular mode or mechanism of interaction. Therefore, as used herein, "treating" includes coating, diffusion, impregnation, grafting, and the like, including any combination thereof as well as any other manner by which the polyphosphazene interacts with the biological tissue.

The specific phosphazene-based polymer poly[bis(trifluoroethoxy) phosphazene] has been found to have good biocompatibility and antithrombotic properties when used to coat a variety of non-biological materials. See German Patent No. DE 196 13 048. See also, for example, U.S. Patent Application Publication Nos. 2003/0157142 A1 and 2005/0136093 A1, the entireties of which are hereby incorporated by reference. This disclosure relates to the use of phosphazene-based polymers, specifically including poly[bis(trifluoroethoxy) phosphazene], to treat biological materials used for bioprosthetic heart valves.

The bioprosthetic heart valves of this invention include any valve that incorporates biological tissue, including the "graft-type," in which substantially the entire valve is grafted from another individual; and the "tissue-type," which are constructed with natural-tissue parts, such as valve leaflets. For example, in this aspect, a bioprosthetic heart valve may be made from mammalian heart valves, mammalian pericardium, mammalian vascular grafts, other mammalian organs, and the like. For example, mammalian organs include human, bovine, or porcine heart. Therefore, generally, the bioprosthetic heart valve comprises either a biological heart valve or a biological tissue adapted as a heart valve.

In some preferred embodiments of the present invention, bioprosthetic heart valves are treated and in some aspects coated with a preferred polyphosphazene represented by formula (I)

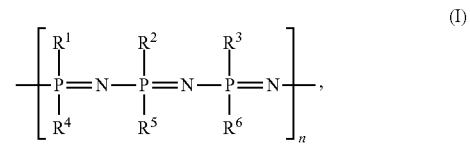

wherein n is 2 to ∞, and $R^1$ to $R^6$ are groups which are each independently variable and are each selected independently from alkyl, aminoalkyl, haloalkyl, thioalkyl, thioaryl, alkoxy, haloalkoxy, aryloxy, haloaryloxy, alkylthiolate, arylthiolate, alkylsulphonyl, alkylamino, dialkylamino, heterocycloalkyl comprising one or more heteroatoms selected from nitrogen, oxygen, sulfur, phosphorus, or a combination thereof or heteroaryl comprising one or more heteroatoms selected from nitrogen, oxygen, sulfur, phosphorus, or a combination thereof, or other similar groups consistent with the intended use. By indicating that n can be as large as ∞ in formula (I), it is intended to specify values of n that encompass polyphosphazene polymers that can have an average molecular weight of up to about 75 million Daltons. For example, in one aspect, n may vary from at least about 100 to about 100,000. In another aspect, by indicating that n can be as large as ∞ in formula (I), it is intended to specify values of n from about 4,000 to about 50,000, more preferably, n is about 7,000 to about 40,000 and most preferably n is about 13,000 to about 30,000.

In another aspect, by indicating that n can be as large as ∞ in formula (I), it is intended to specify values of n that encompass polyphosphazene polymers in which the molecular weight is at least about 70,000 g/mol. In another aspect, n can be selected such that the average molecular weight is at least about 1,000,000 g/mol. Further, n can be selected such that the average molecular weight is at least about 10,000,000 g/mol. In yet another aspect, a useful range of average molecular weights is from about $7\times10^6$ g/mol to about $25\times10^6$ g/mol.

The pendant side groups $R^1$ to $R^6$ are each independently variable and therefore can be the same or different. Further, $R^1$ to $R^6$ can be substituted or unsubstituted. In one aspect, for example, at least one of the groups $R^1$ to $R^6$ can be an unsubstituted alkoxy group, such as ethoxy ($OCH_2CH_3$) or n-propoxy ($OCH_2CH_2CH_3$). In another aspect, for example, at least one of the substituents or groups $R^1$ to $R^6$ is an alkoxy moiety substituted with at least one fluorine atom. Moreover, when $R^1$ to $R^6$ is an alkoxy group, complete substitution of the hydrogen atoms by fluorine atoms can occur such that the alkoxy group is perfluorinated. Examples of useful fluorine-substituted alkoxy groups $R^1$ to $R^6$ include, but are not limited to $OCF_3$, $OCH_2CF_3$, $OCH_2CF_2CF_3$, $OCH(CF_3)_2$, $OCCH_3(CF_3)_2$, $OCH_2CF_2CF_2CF_3$, $OCH_2(CF_2)_3CF_3$, $OCH_2(CF_2)_4CF_3$, $OCH_2(CF_2)_5CF_3$, $OC_{1-2}(CF_2)_6CF_3$, $OCH_2(CF_2)_7CF_3$, $OCH_2CF_2CHF_2$, $OCH_2CF_2CF_2CHF_2$, $OCH_2(CF_2)_3CHF_2$, $OCH_2(CF_2)_4CHF_2$, $OCH_2(CF_2)_5CHF_2$, $OCH_2(CF_2)_6CHF_2$, $OCH_2(CF_2)_7CHF_2$, and the like. The groups $R^1$ to $R^6$ also can be haloalkoxy groups, which can include fluoro-, chloro-, bromo-, and/or iodo-substituted alkoxy groups.

In another aspect $R^1$ to $R^6$ of formula (I) can be selected independently from alkyl groups, or from other substituents that comprise alkyl groups, such alkoxy, alkylsulphonyl, aminoalkyl, haloalkyl, thioalkyl, and the like. In this aspect any alkyl group can be, for example, straight or branched chain alkyl groups having from 1 to about 20 carbon atoms, it being possible for the alkyl groups to be further substituted, for example, by at least one halogen atom, such as a fluorine atom or other functional group such as those noted for the $R^1$ to $R^6$ groups above. By specifying alkyl groups such as propyl or butyl, it is intended to encompass any isomer of the particular alkyl group.

Examples of alkoxy groups include, but are not limited to, methoxy, ethoxy, propoxy, and butoxy groups, which can also be further substituted by at least one fluorine atom, with 2,2,2-trifluoroethoxy groups being preferred.

Examples of alkylsulphonyl groups include, but are not limited to, methylsulphonyl, ethylsulphonyl, propylsulphonyl, and butylsulphonyl groups.

Examples of dialkylamino groups include, but are not limited to, dimethyl-, diethyl-, dipropyl-, and dibutylamino groups.

Exemplary aryloxy groups include, for example, compounds having one or more aromatic ring systems having at least one oxygen atom, non-oxygenated atom, and/or rings having alkoxy substituents, it being possible for the aryl group to be substituted for example by at least one alkyl or alkoxy substituent defined above. Examples of aryloxy groups include, but are not limited to, phenoxy and naphthoxy groups, and derivatives thereof including, for example, substituted phenoxy and naphthoxy groups.

The heterocycloalkyl group can be, for example, a ring system which contains from 3 to 10 atoms, at least one ring atom being a nitrogen, oxygen, sulfur, phosphorus, or any combination of these heteroatoms. The hetereocycloalkyl group can be substituted, for example, by at least one alkyl or alkoxy substituent as defined above. Examples of heterocycloalkyl groups include, but are not limited to, piperidinyl, piperazinyl, pyrrolidinyl, and morpholinyl groups, and substituted analogs thereof.

The heteroaryl group can be, for example, a compound having one or more aromatic ring systems, at least one ring atom being a nitrogen, an oxygen, a sulfur, a phosphorus, or any combination of these heteroatoms. The heteroaryl group can be substituted for example by at least one alkyl or alkoxy substituent defined above. Examples of heteroaryl groups include, but are not limited to, imidazolyl, thiophene, furane, oxazolyl, pyrrolyl, pyridinyl, pyridinolyl, isoquinolinyl, and quinolinyl groups, and derivatives thereof.

In another aspect of the present invention, the bioprosthetic heart valve is treated, and optionally coated, with poly[bis(trifluoroethoxy)phosphazene].

In yet another aspect of this invention, a bioprosthetic implant includes a biological tissue and a polyphosphazene such as a poly[bis(trifluoroethoxy)phosphazene] polymer applied to the biological tissue. The biological tissue may include a heart valve, pericardium, vascular graft, shunt, or bodily organ, particularly a mammalian heart valves, mammalian pericardium, mammalian vascular grafts, or mammalian organs. Examples include human, bovine, or porcine heart valves; human, bovine, or porcine pericardium; human, bovine, or porcine vascular grafts; or human, bovine, or porcine organs.

The bioprosthetic heart valve of this invention is treated with a polyphosphazene in any manner that allows the polyphosphazene to contact the biological material and interact in some manner such that some polyphosphazene is retained in or on the treated heart valve. In one aspect, the method of treating the biological material typically includes the steps of combining a polyphosphazene polymer, a fixing agent, a surfactant, and a solvent in which the polyphosphazene is at least partially soluble to form a solution, and applying the solution to the bioprosthetic implant. A variety of organic solvents are suitable for the preparation of the polyphosphazene solution including polar organic solvents. In one aspect, solvents that show some solubility in or miscibility with water are suitable, for example, acetone, tetrahydrofuran, and the like. For a spraying application volatile ether solvents such as dimethyl ether are suitable.

For example, suitable solvents include, but are not limited to, ethyl acetate, propyl acetate, butyl acetate, pentyl acetate, hexyl acetate, heptyl acetate, octyl acetate, acetone, methylethylketone, methylpropylketone, methylisobutylketone, tetrahydrofuran, cyclohexanone, diglyme, t-butyl methyl ether, dimethyl ether, hexafluorobenzene, tetramethyl urea, tetramethyl guanidine, dimethyl acetamide and the like, including any combinations thereof. Also, mixtures of these solvents may be used, or any solvent may be supplemented with the addition of other solvents or nonsolvents, such as ethane, propane, butane, pentane, hexane, heptane, toluene, benzene, xylene(s), mesitylene, diethyl ether, water and the like. In yet another aspect, a supercritical solution of a polyphosphazene in suitable solvents, such as carbon dioxide or dimethyl ether is created at a specific set of temperature and pressure parameters and used to treat the substrates in question.

Further, other components may be added to the polyphosphazene solution, examples of which include, but are not limited to, co-solvents to adjust solubility, surfactants, dispersants, emulsifying agents, fillers, stabilizers, dyes, pigments, wetting, leveling or stratisfying agents, adhesion agents, and the like, including any combination thereof. The polyphosphazene solution used to contact with the biological tissue in the bioprosthetic implant typically contains at least one compound with general formula (I) in a concentration of from about 0.1% to about 99%, in the solvent.

The polyphosphazene may be applied to the bioprosthetic implant by any method or in any manner. As used herein, the term "applied" means "contacted" in any manner and is used without regard to any particular mechanism or reaction by which the polymer may interact with the heart valve it is applied to. Thus, the polyphosphazene may be applied by any treatment as noted herein and/or a coating. A preferred polyphosphazene polymer of the present invention is poly[bis (trifluoroethoxy)phosphazene]. The time and temperature of the treatment of the biological tissue with the polyphosphazene are not critical in this invention, but may be adapted to meet the specific requirements of the desired application.

For example, the contact time between the polyphosphazene and biological material may range from about 1 second to several days. In this aspect, for example, contact time may range from about 20 seconds to about 3 days, from about 1 minute to about 1 day, from about 3 minutes to about 6 hours, or from about 5 minutes to about 3 hours. The temperature of the treatment step is also not critical, as long as the temperature is suitable for the biological tissue. For example, the bioprosthetic implant may be contacted by immersing in a solution of the polyphasphazene, immediately removed, then allowed to air dry as the solvent evaporates. In this case, contact time with the solution will depend primarily upon the volatility of the solvent. In another aspect, the bioprosthetic implant may be contacted by immersing in a solution of the polyphasphazene and maintained in the solution for a period of time prior to removing and allowing to dry. In this case, contact time with the solution will depend upon the time the implant is maintained in the solution as well as the volatility of the solvent. Thus, the polyphosphazene may be applied to the bioprosthetic implant by any method.

Typically, a temperature is selected that is high enough for the particular contact time selected, such that the polyphosphazene can interact with the biological material sufficiently to be retained in or on the treated heart, yet not so high as to adversely affect the biological material. For example, in this aspect, contact temperatures can range from about 4° C. to about 50° C., from about 10° C. to about 40° C., or from about 15° C. to about 37° C. Typically, the contact times depend on the evaporation rate of the solvent. In one aspect, preferred contact temperature is about room temperature, that is, between about 18° C. and about 24° C. In another aspect, contact time of about 3 to about 5 minutes and a temperature of about room temperature works well. If an implant should be cooled, contact temperatures as low about 3° C. to about 4° C. can be used. In this aspect, contact temperatures from about 4° C. to about 37° C. are suitable.

Examples of fixing agents can include various functional organic solvents, examples of which include, but are not limited to, aldehydes, amines, polyamines, aminosilanes, and the like. Examples of aldehydes include, but are not limited to, formaldehyde, glutaraldehyde, acetaldehyde, propionaldehyde, 2-methyl-propionaldehyde, butyraldehyde, isobutyraldehyde, 2-methylbutyraldehyde, 2-ethylbutyraldehyde, valeraldehyde, 2-methylvaleraldehyde, 1,6-hexanedial, hexyldehyde, 2-ethylcaproaldehyde, heptaldehyde, octaldehyde, nonaldehyde, decaldehyde, undecaldehyde, dodecaldehyde, or any combination thereof. Combinations of fixing agents including combinations of aldehydes can be used. While not intending to be bound by theory, it is thought that the method of action of an aldehyde fixing agent is the polycondensation reaction of aldehydes under loss of water, or the condensation between amines and aldehydes to form amides, for example the combination of a poly(ethylene imine) and an aldehyde may form a crosslinked, stable interface.

Examples of aminosilane fixing agents include, but are not limited to, (3-aminopropyl)triethoxysilane, (3-aminopropyl) trimethoxysilane, N-(2-aminoethyl)-3-aminopropyltrimethoxysilane, bis[(3-trimethoxysilyl)propyl]ethylenediamine, (3-trimethyloxysilylpropyl)diethylenetriamine, and the like. In addition, ureido-terminated silanes and glycidylterminated silanes can serve as suitable fixing agents. Examples of ureido-terminated silanes include, but are not limited to, γ-ureidopropyltrimethoxy silane and γ-ureidoethyltrimethoxy silane. Examples of glycidyl-terminated silanes include, but are not limited to, 3-(glycidoxypropyl)triethoxysilane, 3-(glycidoxypropyl)trimethoxysilane, and 3-(glycidoxypropyl)dimethylethoxysilane, and 3-(glycidoxypropyl)methyldimethoxysilane.

In still another aspect, the polyphosphazene soluble organic solvent can be an aldehyde and act as a fixing agent. In a further aspect the dissolution of a polyphosphazene can be effected in a specifically suited solvent, such as dimethoxymethane (monoglyme) or trimethyl orthoformate, which may hydrolyze under acidic condition to form formaldehyde in situ, thereby fixating the tissue in question, and in parallel precipitating the polyphosphazene onto and respectively impregnating the tissue.

Surfactants may be anionic, cationic, or zwitterionic, as long as the surfactant is compatible with the overall composition. For example, useful surfactants include, but are not limited to, a polysorbate, a poloxamer, glycerol, polyethylene imines, chitosans, polyallylamines, polyvinyl pyrrolidone, PVP, DEAE dextran, and the like, including combinations thereof.

In addition, the polyphosphazene may be used in combination with, or alternatively without, a monomeric, oligomeric or polymeric adhesion promoter, a tie layer, a surfactant, a dispersing agent, a filling agent a stabilizing agent, or any other agent targeted at improving the interfacial compatibility and/or stability between the polyphosphazene and the bioprosthetic implant when contacting each other. Such interfacial compatibility and/or stability assists in achieving the desired biomedical and mechanoelastic performance.

In yet another aspect, the bioprosthetic implant may be coated with a polyphosphazene by pre-forming a polyphosphazene membrane and then applying the membrane to the bioprosthetic implant, or contacting the polyphosphazene with the bioprosthetic implant. The membrane may be applied using adhesion promoters as described herein, or alternatively by applying a tissue adhesive, which bonds to the polyphosphazene as well, or by simply solvent welding the membrane to the substrate wherein the solvent modifies the surface of the substrate in a manner that the membrane will bind favorably to the substrate. Examples of forming a membrane of a polyphosphazene are provided in U.S. Pat. No. 7,265,199, the entirety of which is hereby incorporated by reference. While not bound by theory, it is believed that a semi-interpenetrating network between the two components may be formed. However, this invention encompasses any combination of a bioprosthetic implant and polyphosphazene, including a pre-formed polyphosphazene membrane that is applied to a bioprosthetic implant, regardless of any mechanism by which the polyphosphazene and the bioprosthetic implant might interact.

Once the polyphosphazene and the biological tissue have been contacted, the solvent and remaining volatiles can be evaporated without any additional measures. In this aspect, for example, the solvent vapor concentration over the substrate is optimally set in a controlled manner, as is also the pressure and the temperature. The pressure and temperature of the drying step is also not critical, as long as the pressure and temperature are suitable for the biological tissue.

In yet a further aspect, the present invention features a method of treating a bioprosthetic heart valve that includes the steps of contacting the heart valve tissue with a polyphosphazene represented by formula (I) as provided herein. This aspect can further include coating the tissue with the polyphosphazene and/or impregnating, that is fill in part or throughout, or permeate through or into, the tissue with the polyphosphazene. Thus, this disclosure also provides a method of improving the antithrombogenic, biocompatibility, or hemocapatibility properties of a bioprosthetic heart valve, comprising contacting the bioprosthetic heart valve with a polyphosphazene of formula (I) indicated above, wherein the polyphosphazene is coated, diffused, impregnated, grafted, or any combination thereof, into or onto the bioprosthetic heart valve.

The present invention is applicable to any tissue-type bioprosthetic heart valve comprising assemblies having various amounts, even small amounts, of biological material. For example, some of these valves include only the leaflets derived from natural material such as porcine or bovine or other mammalian sources, with synthetic annular structures or stents that support the valve. In other valves, both the leaflets and the annular support ring are formed of biopolymers such as collagen and/or elastin. All these valves, including the biopolymer valves and the so-called stented valves that contain a stent and a biological valve member, are applicable to this invention. Moreover, there is no limitation as to the particular biological tissue that may be used, although typically tissue is harvested from heart valves or from the Pericardial Sac of bovine, equine, or porcine. Thus, examples of biological tissues that can be used in the heart valve tissue described above may include mammalian pericardium, mammalian heart valves, mammalian vascular graft, or mammalian organs such as heart.

Examples of devices that apply to human and other animal tissue-type bioprostheses are found in U.S. Pat. Nos. 3,656, 185 and 4,106,129. Two examples of currently manufactured and marketed tissue-type valves are the MITROFLOW™ Heart Valve by Mitroflow International, Inc., 11220 Voyager Way, Unit 1, Richmond, B.C., Canada V6X 351 and Bovine Pericardial Valve by Sorin Biomedical, S.P.A., 13040 Saluggia (VC), Italy.

In another preferred embodiment of the present invention, a bioprosthetic implant includes a biological tissue and a poly[bis(trifluoroethoxy)phosphazene] polymer applied to the biological tissue. The biological tissue may include any of the biological tissues described above, including a heart valve, a vascular graft, a shunt, or other bodily organs.

A bioprosthetic heart valve coated according to any of the above embodiments may have a coating thickness of from about 1 nm to about 100 µm. In this aspect, the bioprosthetic heart valve may have a coating thickness from about 1 nm to about 10 µm, or from about 1 nm to about 1 µm.

Treatment and/or coating technology methods may include, without limitation, spray coating, dip coating, electrospinning, surface interpenetration network, phase separation, precipitation, and the like. Thus, treatment and/or coating may be accomplished by any method of contacting the bioprosthetic heart valve with the polyphosphazene.

Advantages of the present invention may include improved biocompatibility (e.g., reduced platelet adhesion and protein binding, and non-thrombogenicity), bacterial resistance, anti-restenosis, hemocompatibility, reduction in calcification of biological heart valve tissues, increased tissue durability, and reduction in adverse immune responses to xenografts.

In a further aspect, this invention provides a method of reducing tissue calcification of a mammalian heart valve, and a method of imparting an anti-calcification property to a mammalian heart valve, comprising contacting the mammalian heart valve with a polyphosphazene. In this aspect, the polyphosphazene can be poly[bis(trifluoroethoxy)phosphazene], any other polyphosphazene disclosed herein, or any combination of polyphosphazenes disclosed herein. Further, the polyphosphazene(s) may be coated, diffused, impregnated, grafted, or any combination thereof, into or onto the mammalian heart valve.

Figure 2:
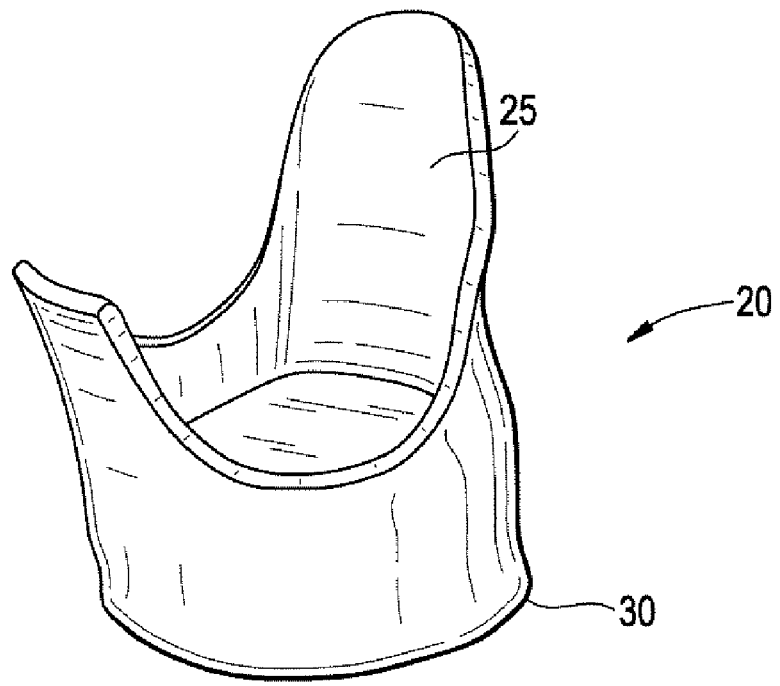
FIG. 2 is a perspective view of a human graft-type (homograft) heart valve that may be treated as disclosed herein.

Examples of various embodiments and aspects of this invention are illustrated in the accompanying figures. For example, FIGS. 1 and 2 present perspective views of two graft-type heart valves that can be used in this invention. FIG. 1 is a perspective view of a porcine graft-type (xenograft) heart valve 5 that can be treated as disclosed herein, with natural leaflets 10 and supporting annular portion 15 illustrated. Similarly, a human graft-type (homograft) heart valve 20 is illustrated in perspective view at FIG. 2. wherein the natural leaflets 25 and supporting annular portion 30 are shown.

Figure 3:
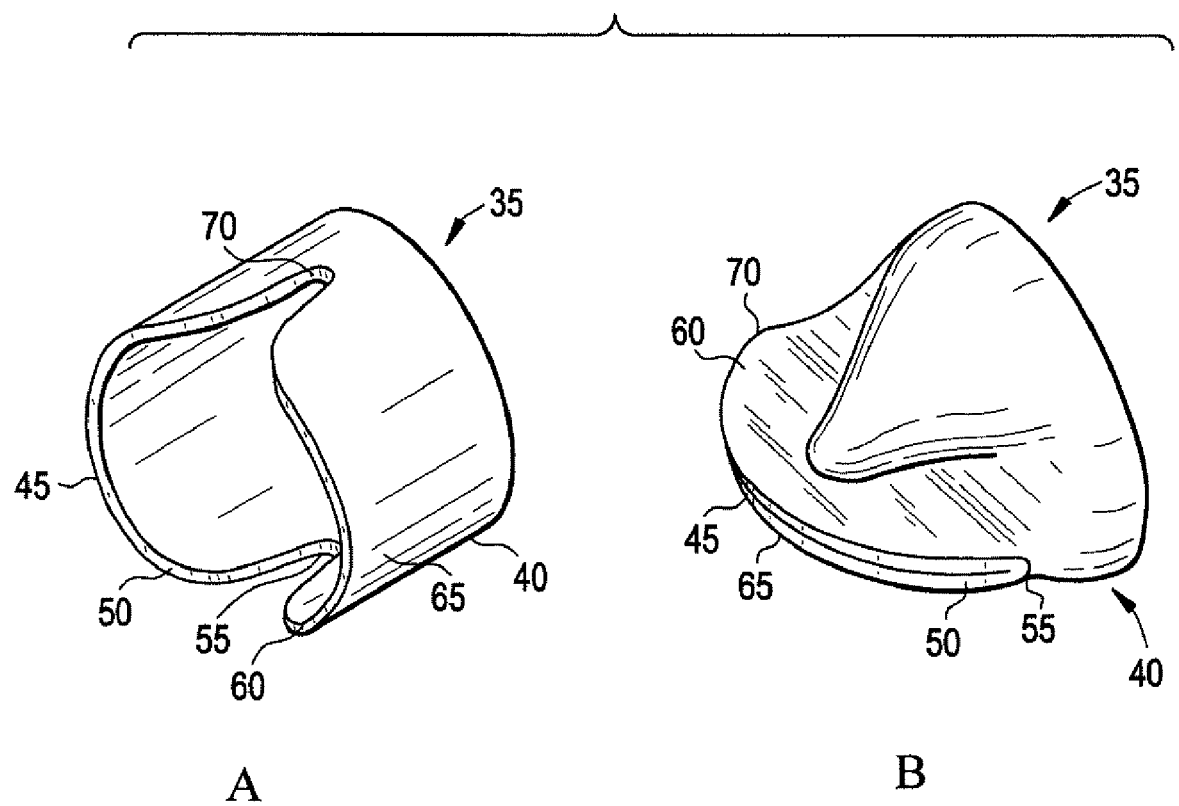
FIG. 3 illustrates an exemplary tissue-type heart valve, presented in open (A) and closed (B) configurations, which may be treated as disclosed herein.

FIG. 3 shows an exemplary tissue-type heart valve 35, presented in open and closed configurations. In FIG. 3A, the open tubular valve and supporting annular portion 40 has flexible junctures or creases 45, 50, 55, 60, 65, and 70. FIG. 3B is a perspective view of the valve depicted in FIG. 3A in the closed position, showing the supporting annular portion 40 and flexible junctures or creases 45, 50, 55, 60, 65, and 70 as illustrated in open form in FIG. 3A.

Figure 4:
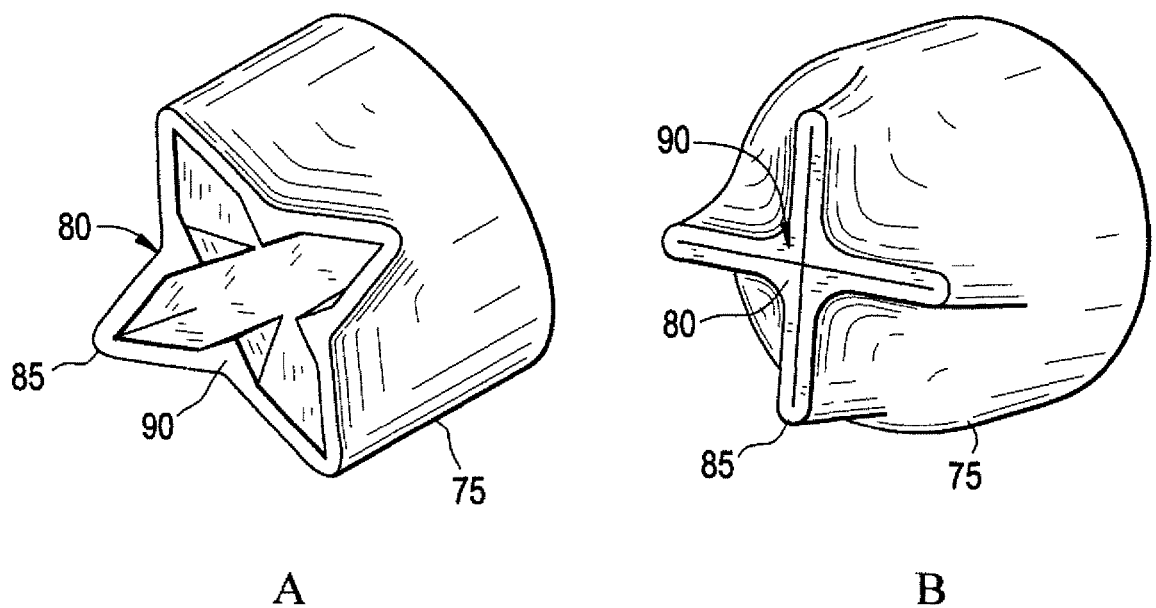
FIG. 4 illustrates an a further example of a tissue-type heart valve, presented in open (A) and closed (B) configurations, which may be treated as disclosed herein.

FIG. 4 presents another embodiment of the present invention. In FIG. 4A, tubular valve 75 is in the open position and has flexible junctures or creases 80, 85, and extended portion 90. FIG. 4B shows the FIG. 4A embodiment in the closed position depicting flexible junctures 80 and 85 having sufficient support to maintain their relative position while having sufficient flexibility to close, such that mating at the extended portion 90 can occur, thereby shutting off blood flow.

Figure 5:
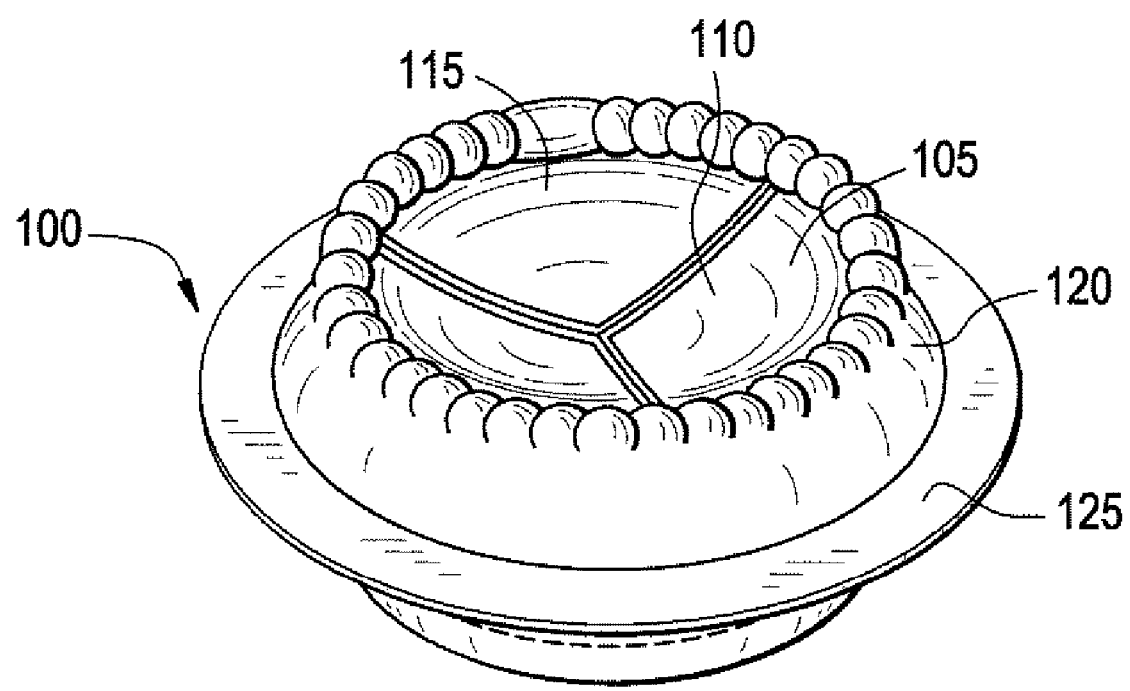
FIG. 5 illustrates yet another example of a tissue-type heart valve that may be treated as disclosed herein, in which the tissue leaflets are attached to a synthetic annular portion suitable for implantation.

FIG. 5 illustrates yet another example of a tissue-type heart valve 100, in which the tissue leaflets are attached to a synthetic annular portion suitable for implantation. In FIG. 5, the bioprosthetic heart valve comprises biological tissue 105 with cusps 110 and envelopes 115 shaped like aortic sinuses, attached to a more rigid annular frame 120 having a cuff 125 for attachment.

It will be appreciated by those skilled in the art that changes can be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

EXAMPLES

Example 1

A heart valve is extracted from a human or other mammal and subjected to a rinse in a dehydrating agent/solvent prior to treatment. The rinsed heart valve is then pre-treated by contacting with fixing agent such as an amine, polyamine, aminosilane, and the like. The pretreated heart valve is then immersed into a solution of solution of poly[bis(trifluoroethoxy)phosphazene] polymer in acetone or THF solvent, after which the treated valve is allowed to dry. Following this coating step, the treated valve is again hydrated and stored in a nutrient or saline solution, and further conditioned, sterilized, stored, and used in a manner according to the use of any graft-type heart valve utilized as a bioprosthetic implant.

Example 2

A poly[bis(trifluoroethoxy)phosphazene] polymer having an average molecular weight of from about $10 \times 10^6$ g/mol to about $2 \times 10^7$ g/mol is prepared according to U.S. Patent Application Publication No. 2003/0157142. A solution of the poly[bis(trifluoroethoxy)phosphazene] that contains the polyphosphazene in a concentration from about 0.1% to about 99% is prepared in a solvent such as methylethylketone, along with a fixing agent such as formaldehyde or glutaraldehyde and a surfactant. The surfactant may be selected from a polysorbate or a poloxamer, a polyethylene imine, or a polyallylamine, and the like, as disclosed herein. Alternatively, formaldehyde or glutaraldehyde may serve as the solvent and the fixing agent without the need for an additional solvent, as described herein. Also alternatively, either the solvent or the fixing agent may also serve as a surfactant, without the need for additional surfactant.

A porcine graft-type heart valve is dipped into the poly[bis(trifluoroethoxy)-phosphazene] solution and maintained in the solution for about 5 minutes to about 20 minutes, removed from the solution, and allowed to air dry at room temperature (roughly 23° C.) and atmospheric pressure so as to substantially remove the poly[bis(trifluoroethoxy)phosphazene] solution volatile components. The valve is then be conditioned, sterilized, stored, and used in a manner according to the use of any porcine graft-type heart valve that is utilized as a bioprosthetic implant.

Example 3

A pressurizable container, such as a lecture bottle, pressure tin, or autoclave, closed with a brass body, mini gas regulator, and containing about 250 mL/150 g of dimethyl ether, is cooled externally with a solid $CO_2$/ethanol cooling bath (or alternatively, with a liquid $N_2$ bath) to a temperature to below its boiling point (−23° C.) but above its melting temperature (−138.5° C.). Using proper safety precautions (protecting screen/shield, ventilation), the gas regulator is opened after internal pressure has been equalized to atmospheric pressure by slowly opening the valve, and the regulator is then removed. A solid sample of poly[bis(trifluoroethoxy)phosphazene] polymer, 1.25 g, (0.5% w/v) is quickly added to the contents of the container, and the pressurizable container is then sealed airtight. The polyphosphazene sample is then dissolved in the dimethyl ether over a time period of 24 hours at room temperature, using a horizontal shaker to agitate the contents of the pressurized bottle.

A porcine heart valve is extracted from a donor animal and subjected to fixation using glutaraldehydate/formaldehyde, in the manner known by one of ordinary skill in the art, or by the methods disclosed herein. The implant is then treated with additional surfactants and/or adhesion promoters if desired, as described above.

Using the pressurized container valve, the heart valve sample is coated from all sides using the prepared poly[bis(trifluoroethoxy)phosphazene] spray container. The progress of coating is monitored by measuring contact angles with a Wilhelmy balance or an elipsometer. For surgical and practical procedures, the progress is also evident from the water-repellant properties imparted to the implant.

Example 4

A poly[bis(trifluoroethoxy)phosphazene] polymer is prepared and applied to a human graft-type (homograft) heart valve such as that illustrated in FIG. 2, according to any of Examples 1-3. Once treatment of the bioprosthetic heart valve is completed, the valve may then be used in a manner according to the use of any human graft-type heart valve that is utilized as a bioprosthetic implant.

Example 5

A poly[bis(trifluoroethoxy)phosphazene] polymer is prepared and applied to a tissue-type heart valve, such as that illustrated in FIG. 3 or 4, or a heart valve comprising tissue leaflets and a synthetic annular portion and frame as illustrated in FIG. 5, according to any of Examples 1-3. Once treatment of the bioprosthetic heart valve is completed, the valve may then be used according to the manner in which any heart valve of that particular type is utilized as a bioprosthetic implant.

We claim:

1. A bioprosthetic heart valve comprising a biological tissue and a polyphosphazene represented by formula (I):

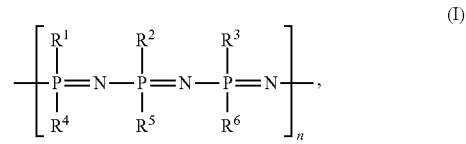

wherein n is 2 to ∞; and $R^1$ to $R^6$ are groups which are each selected independently from alkyl, aminoalkyl, haloalkyl, thioalkyl, thioaryl, alkoxy, haloalkoxy, aryloxy, haloaryloxy, alkylthiolate, arylthiolate, alkylsulphonyl, alkylamino, dialkylamino, heterocycloalkyl comprising one or more heteroatoms selected from nitrogen, oxygen, sulfur, phosphorus, or a combination thereof or heteroaryl comprising one or more heteroatoms selected from nitrogen, oxygen, sulfur, phosphorus, or a combination thereof.

2. The bioprosthetic heart valve of claim 1, wherein at least one of $R^1$ to $R^6$ is an alkoxy group substituted with at least one fluorine atom.

3. The bioprosthetic heart valve of claim 1, wherein the polyphosphazene is poly[bis(trifluoroethoxy)phosphazene].

4. The bioprosthetic heart valve of claim 1, wherein the polyphosphazene is coated, diffused, impregnated, grafted, or any combination thereof, into or onto the biological tissue.

5. The bioprosthetic heart valve of claim 1, wherein the polyphosphazene is coated onto the biological tissue at a thickness of from about 1 nm to about 100 μm.

6. The bioprosthetic heart valve of claim 1, wherein the polyphosphazene has an average molecular weight of about 10 to about 13 million Daltons.

7. The bioprosthetic heart valve of claim 1, wherein the biological tissue comprises at least one of a mammalian heart valve, a mammalian pericardium, or a mammalian vascular graft.

8. A method of manufacturing a bioprosthetic heart valve, comprising providing a biological tissue; and contacting the biological tissue with a polyphosphazene of formula (I):

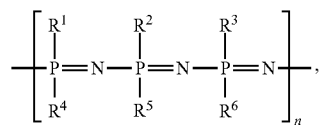

wherein n is 2 to ∞; and $R^1$ to $R^6$ are groups which are each selected independently from alkyl, aminoalkyl, haloalkyl, thioalkyl, thioaryl, alkoxy, haloalkoxy, aryloxy, haloaryloxy, alkylthiolate, arylthiolate, alkylsulphonyl, alkylamino, dialkylamino, heterocycloalkyl comprising one or more heteroatoms selected from nitrogen, oxygen, sulfur, phosphorus, or a combination thereof, or heteroaryl comprising one or more heteroatoms selected from nitrogen, oxygen, sulfur, phosphorus, or a combination thereof.

9. The method of claim 8, wherein the polyphosphazene is coated, diffused, impregnated, grafted, or any combination thereof into or onto the biological tissue.

10. The method of claim 8, wherein at least one of $R^1$ to $R^6$ is an alkoxy group substituted with at least one fluorine atom.

11. The method of claim 8, wherein the polyphosphazene is poly[bis(trifluoroethoxy)phosphazene].

12. The method of claim 8, wherein the biological tissue comprises at least one of a mammalian heart valve, a mammalian pericardium, or a mammalian vascular graft.

13. The method of claim 8, further comprising combining the polyphosphazene, a fixing agent, a surfactant, and a polyphosphazene soluble organic solvent to form a polyphosphazene solution prior to contacting the biological tissue with the polyphosphazene solution.

14. The method of claim 13, wherein the polyphosphazene is poly[bis(trifluoroethoxy)phosphazene].

15. The method of claim 13, wherein the fixing agent is selected from formaldehyde, glutaraldehyde, or a combination thereof.

16. The method of claim 13, wherein the surfactant is selected from a polysorbate, a poloxamer, glycerol, polyethylene imines, chitosans, polyallylamines, polyvinyl pyrrolidone, PVP, DEAE dextran, or a combination thereof.

17. A method of improving the antithrombogenic, biocompatibility, or hemocapatibility properties of a bioprosthetic heart valve, comprising:

contacting the bioprosthetic heart valve with a polyphosphazene of formula (I):

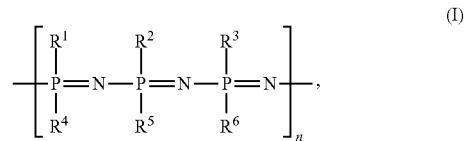

wherein n is 2 to ∞; and $R^1$ to $R^6$ are groups which are each selected independently from alkyl, aminoalkyl, haloalkyl, thioalkyl, thioaryl, alkoxy, haloalkoxy, aryloxy, haloaryloxy, alkylthiolate, arylthiolate, alkylsulphonyl, alkylamino, dialkylamino, heterocycloalkyl comprising one or more heteroatoms selected from nitrogen, oxygen, sulfur, phosphorus, or a combination thereof, or heteroaryl comprising one or more heteroatoms selected from nitrogen, oxygen, sulfur, phosphorus, or a combination thereof;

wherein the polyphosphazene is coated, diffused, impregnated, grafted, or any combination thereof, into or onto the bioprosthetic heart valve.

18. The method of claim 17, wherein the polyphosphazene is coated onto the bioprosthetic heart valve at a thickness of from about 1 nm to about 100 μm.

19. The method of claim 17, wherein at least one of $R^1$ to $R^6$ is an alkoxy group substituted with at least one fluorine atom.

20. The method of claim 17, wherein the polyphosphazene is a poly[bis(trifluoroethoxy)phosphazene].

21. The method of claim 17, wherein the polyphosphazene has a molecular weight of about 10 to about 13 million Daltons.

22. The method of claim 17, further comprising combining the polyphosphazene, a fixing agent, a surfactant, and a polyphosphazene soluble organic solvent to form a polyphosphazene solution prior to contacting the bioprosthetic heart valve with the polyphosphazene solution;

wherein the polyphosphazene is a poly[bis(trifluoroethoxy)phosphazene];

the fixing agent is selected from formaldehyde, glutaraldehyde, or a combination thereof; and the surfactant is selected from a polysorbate, a poloxamer, glycerol, or a combination thereof.

23. A bioprosthetic heart valve comprising a mammalian heart valve and a poly-[bis(trifluoroethoxy)phosphazene].

24. A method of making a bioprosthetic heart valve comprising providing a mammalian heart valve; and contacting the mammalian heart valve with a poly[bis(trifluoroethoxy)-phosphazene];

wherein the poly[bis(trifluoroethoxy)phosphazene] is coated, diffused, impregnated, grafted, or any combination thereof, into or onto the mammalian heart valve.

* * * * *